Figure 1:
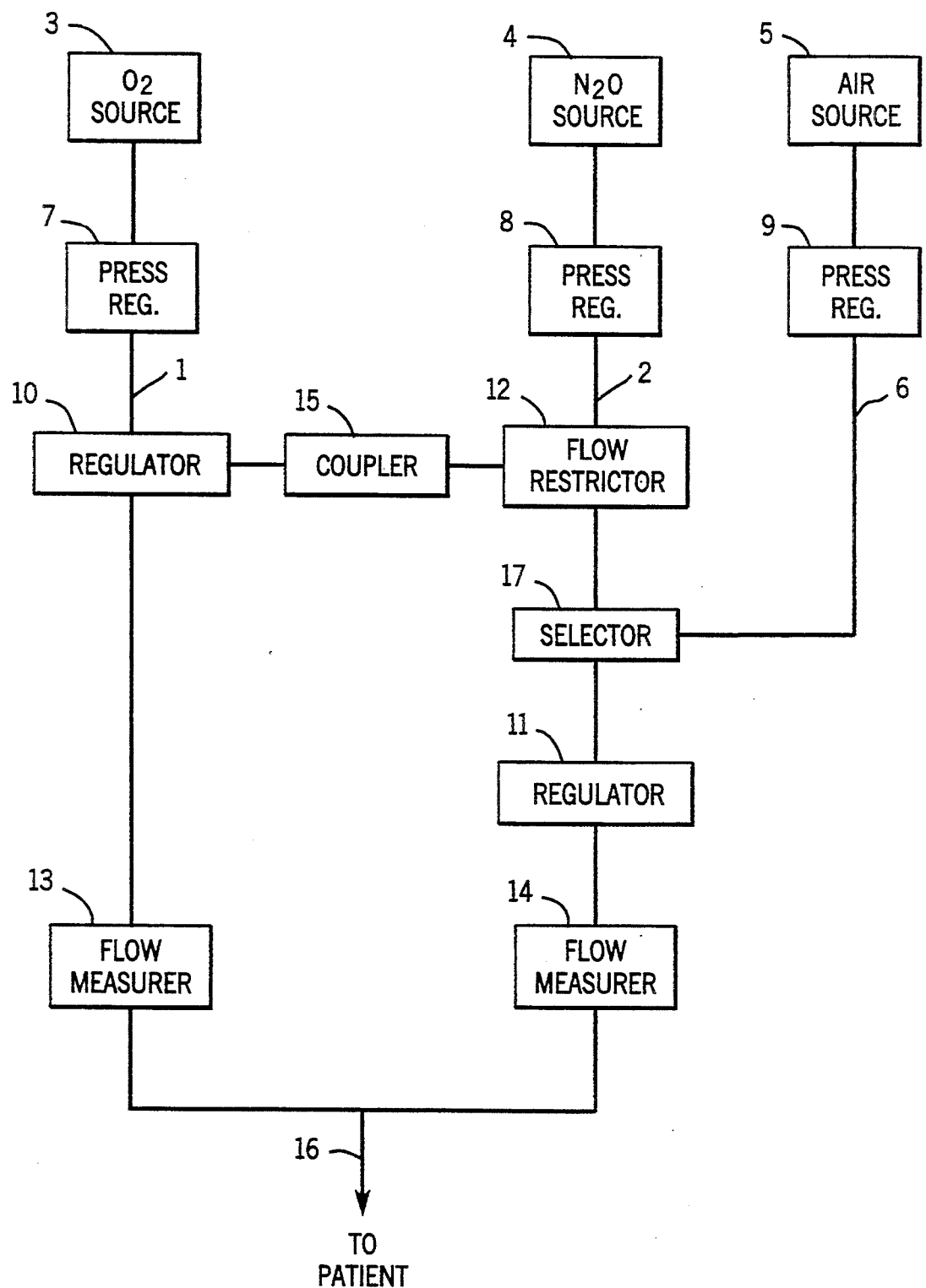

United States Patent [19]

Heinonen

[11] Patent Number: 5,435,332
[45] Date of Patent: Jul. 25, 1995

[54] APPARATUS AND METHOD FOR MIXING TOGETHER GASES FLOWING IN DIFFERENT CHANNELS

[75] Inventor: Erkki Heinonen, Helsinki, Finland

[73] Assignee: Instrumentarium Corp., Finland

[21] Appl. No.: 307,471

[22] Filed: Sep. 16, 1994

Related U.S. Application Data

[63] Continuation of Ser. No. 58,297, May 6, 1993, abandoned.

[30] Foreign Application Priority Data

May 7, 1992 [FI] Finland .................................. 922087

[51] Int. Cl.⁶ ...................... F16K 11/16; F16K 31/53; G05D 11/03
[52] U.S. Cl. ............................................ 137/3; 137/607
[58] Field of Search ...................... 137/3, 595, 606, 607

[56] References Cited

U.S. PATENT DOCUMENTS

| | | | |
|---|---|---|---|
| 3,739,799 | 6/1973 | Bickford et al. | 137/88 |
| 3,809,109 | 5/1974 | Breiling et al. | 137/607 X |
| 4,237,925 | 12/1980 | Urushida | 137/607 X |
| 4,266,573 | 5/1981 | Braatz | 137/607 X |
| 4,546,794 | 10/1985 | Ball | 137/607 |
| 4,549,563 | 10/1985 | Monnier | 137/100 |
| 4,605,034 | 8/1986 | Urushida | 137/607 X |
| 4,685,156 | 8/1987 | Brabazon | 137/607 X |
| 4,840,195 | 6/1989 | Zabrenski | 137/505.42 X |

FOREIGN PATENT DOCUMENTS

| | | |
|---|---|---|
| 0151289 | 11/1987 | Denmark . |
| 0039932 | 9/1985 | European Pat. Off. . |
| 563036 | 11/1923 | France . |
| 2549979 | 7/1983 | France . |
| 0342145 | 1/1972 | Sweden . |
| 1322928 | 7/1973 | United Kingdom . |
| 2076676 | 12/1981 | United Kingdom . |
| 2133714 | 8/1984 | United Kingdom . |
| 2136703 | 9/1984 | United Kingdom . |
| 2136703 | 9/1986 | United Kingdom . |
| 2216807 | 10/1989 | United Kingdom . |
| 2230843 | 10/1990 | United Kingdom . |

*Primary Examiner*—Stephen M. Hepperle
*Attorney, Agent, or Firm*—Andrus, Sceales, Starke & Sawall

[57] ABSTRACT

The invention relates to an apparatus for mixing gases with each other, said apparatus comprising at least two channels (1, 2) for flowing a gas therein and regulating elements (10, 11) fitted in these channels for controlling a flow progressing in the channels. One channel includes a restricting element (12) connected in series with regulating element (11) for adjusting a maximum value for a gas flowing there through, said restricting element being linked through the intermediary of a coupling assembly (15) to regulating element (10) in one channel such that the operations of regulating element (10) and restricting element (12) are linked together.

The invention relates also to a method for combining gases together at a desired ratio, said gases flowing in at least two different channels (1, 2).

28 Claims, 3 Drawing Sheets

APPARATUS AND METHOD FOR MIXING TOGETHER GASES FLOWING IN DIFFERENT CHANNELS

The present application is a continuation application of U.S. patent application, Ser. No. 08/058,297, filed May 6, 1993, and now abandoned.

The present invention relates to an apparatus for mixing gases together, said apparatus comprising at least two channels for flowing a gas therein and control elements coupled with these channels for regulating a flow progressing in the channels. The invention relates also to a method for combining gases together at a desired ratio, said gases flowing in at least two different channels.

Generally, a fresh gas mixture used during anaesthesia consists of oxygen and an oxide of nitrogen ($N_2O$). The mixing ratio is regulated by controlling the flow rates of such gases. The essential point with respect to anesthetizing a patient is that the gas mixture contains in all conditions a sufficient amount of oxygen. A typical minimum oxygen content is 25%.

The control apparatus for gas flows must include separate regulating devices provided with adjusting knobs for oxygen and $N_2O$ flows as well as separate measurements for gas flows. In addition, its structure must be capable of eliminating a possibility of a hypoxic mixture.

The apparatus must have a structure capable of eliminating the creation of a hypoxic mixture caused by a fall in the oxygen supply pressure or by an operating error. An example of a typical operating error is the closing of an oxygen valve prior to an $N_2O$ valve or the opening of an $N_2O$ valve prior to an oxygen valve.

The build-up of a hypoxic mixture caused by a fall in supply pressure is generally prevented by shutting off the flow of an $N_2O$ channel upon an excessive fall in the pressure of an oxygen channel by means of a so-called "fail safe" valve. The elimination of an operating error can be achieved by a plurality of methods:

The "fail safe" valve has been developed further to provide a pneumatic differential pressure comparator (EP-A-0039932). The apparatus eliminates a hypoxic mixture resulting both from a fall in the oxygen input pressure and an operating error. In the above-cited solution, the oxygen and $N_2O$ flows can be adjusted independently of each other. The flows are delivered through throttles for generating proportional pressures in the flows. The pressures are separated from each other by means of a flexible diaphragm. The diaphragm is provided with a $N_2O$-channel shut-off valve, which monitors the diaphragm movement resulting from a pressure difference between the oxygen and $N_2O$ channels. As the $N_2O$ flow rate increases, the diaphragm deforms towards the oxygen channel. This moves the $N_2O$-channel shut-off valve towards a closed position causing a decrease in the $N_2O$ flow.

A problem in the method is the expensive price caused by the structural complexity and it requires a lot of calibration as a result of deformations in the flexible diaphragm. In addition, on minor gas flows the actual operation of the apparatus is unreliable due to minor pressures developed by the throttles. Securing a reliable operation on minor flows requires special arrangements for shutting off the $N_2O$ flow completely in view of preventing the use of this particular gas.

The problem of minor flows has been solved by providing the above apparatus with a separate, individually openable flow channel in parallel relationship with the $N_2O$-channel shut-off valve (GB 2216807 A). However, the method does not eliminate the possibility of a patient receiving a hypoxic gas, even 100% $N_2O$.

In a solution disclosed in U.S. Pat. No. 4,266,573, the oxygen and $N_2O$ regulating devices are mechanically linked with each other and provided with calibratable motion controls. The $N_2O$ flow can be increased without varying the oxygen flow until the motion control is switched on, whereafter a further increase of the $N_2O$ flow will also result in an increased oxygen flow. The control mechanism operates in a similar fashion when decreasing the oxygen flow. After switching on the control, a decrease of the oxygen flow also decreases the $N_2O$ flow. The switch-on point of a motion control determines a minimum oxygen content, depending on the employed regulating valves, the supply pressure of gases, the gear ratio of a mechanical assembly, as well as the calibration of controls.

In each of the above-described solutions the coupling of gas-flow channels is always on. Thus, the mechanisms are not applicable to an operation that requires the by-pass of this coupling. For example, it is often desirable to mix air instead of $N_2O$ with oxygen. The coupling will be detrimental whenever the gas should contain clean air. In the above solution, the use of air requires a separate flow control means. This again leads to a bulkier and more complicated service connection. The advantage offered by a third adjusting knob for the simultaneous mixing of all three gases is practically unnecessary and even disallowed in some countries, which additionally requires a separate gas selecting function.

When a regulating valve fitted in the oxygen channel is mechanically coupled to switch the same way as a valve in the $N_2O$ channel, the result will be a mixture having a minimum oxygen content (U.S. Pat. No. 4,546,794, DE 3,310,858). The content can be set by the relative opening ratio of said valves. For example, the ratio 1:3 provides a minimum oxygen content of 25% when the valves and gases have identical supply pressures. Oxygen contents higher than this are obtained when the above oxygen-channel regulating valve is accompanied by another regulating valve, fitted with an adjusting knob, intended for the actual oxygen flow and adapted to open and close independently. Due to the apparatus construction, a change in the $N_2O$ flow always brings about a change in the oxygen flow, the latter change being one fourth of the change of $N_2O$ flow. If it is desirable to further diminish the oxygen flow when the oxygen content of a mixture is at minimum, the adjustment must be effected by setting the $N_2O$ regulating valve towards a closed position. This means that the apparatus will be non-ergonomic to operate.

An object of this invention is to eliminate the above problems. An object is to provide a method and apparatus for the combining at a desired ratio, gas flows progressing in at least two different channels. Another object is to provide a simple and low-price method and apparatus for the combination at a desired ratio of gas flows progressing in at least two different channels. A further object is to provide a method and apparatus for the combination at a desired ratio of even minor gas flows progressing in at least two different channels. Yet another object is to provide such an apparatus for the combination of gas flows at a desired ratio, which facilitates the arrangement of gas channels extending from three different gas sources such that the number of flow-regulating elements need not be increased from the number that is necessary when gases are supplied from just two different gas sources. A particular object is to provide a method and apparatus for the combination at a desired ratio of gas flows progressing in at least two different channels to be respirated by a patient, one flow containing oxygen and the combination being such that a minimum oxygen content of a gas respired by a patient is secured.

In a solution of the invention, a flow occurring along two different gas channels is controlled in one channel by means of a flow-regulating element and in the other channel by means of a flow-restricting element, which are coupled together and, thus, the sizes of flow ports to be adjusted thereby are subjected to a substantially simultaneous change. The opening ratios of a regulating element and a restricting element during the regulation of flows may vary either equally to or differently from each other. Thus, the size of gas-flow ports to be controlled by means of a regulating element and a restricting element can be varied in each channel even individually despite the fact that the adjustment thereof occurs simultaneously. Thus, according to this principle, the flow occurring through both channels is adjusted in the same direction in an effort to control the flow through both channels, but said flows need not necessarily have equal flow rates. However, the relative proportions of flows in different channels should preferably be maintained constant, even if the intensity of flow is changed.

Also according to the invention, the channel extending by way of said restricting element is further fitted with a regulating means capable of reducing a flow otherwise occurring through the restricting element located in this same channel. The restricting element, in turn having the adjustment of its flow port coupled with the adjustment of the flow port of a regulating element fitted in the neighboring flow channel, restricts a flow progressing there through to its maximum value or rate.

A regulating element and a restricting element located in different gas channels are preferably linked mechanically together. Thus, through the action of a mechanical link or coupling it is possible to operate a single control button for opening and closing a flow occurring through both the regulating element and the restricting element until a desired flow is obtained. An effort is made to achieve a desired flow first in the gas channel provided with a mechanically coupled regulating element. In the other flow channel, the size of a flow port included in the restricting element is preferably such that a flow passing there through is sufficient in relation to said first flow channel to be controlled through the action of mechanical coupling. Thus, the flow port of said restricting element allows at its maximum a tolerably intensive flow that can be reduced, if necessary, by means of a regulating means fitted in the same channels.

The invention is particularly suitable for the regulation of respiratory gases delivered to a patient, e.g. in anaesthesia. The vital gas, i.e. oxygen, is delivered to a patient preferably along a channel fitted with a regulating element, said regulating element being in turn coupled with a restricting element which is again fitted in a parallel channel, generally used for flowing an oxide of nitrogen, such as $N_2O$. This arrangement is used to guarantee that a patient will definitely receive a sufficient amount of oxygen. The restricting element for flowing the oxide of nitrogen there through cannot be opened without simultaneously opening the oxygen-channel regulating element. On the other hand, the oxygen channel cannot be closed without closing the nitrogen oxide channel. Instead, the flow of nitrogen oxide to be supplied to a patient can be independently regulated by operating a regulating means fitted in the nitrogen oxide channel in such a manner, however, that the maximum flow of nitrogen oxide adjusted by means of the restricting element cannot be exceeded. Furthermore, the re-adjustment of oxygen flow effected by means of the regulating element has an automatic effect on the size of a flow port included in the restricting valve located in the nitrogen oxide channel and therefore on the maximum rate of nitrogen oxide flow and vice versa.

The regulating element can be a valve, e.g. a needle valve, for controlling a flow progressing there through when ever necessary. The restricting element can also be a valve. It can be a needle valve identical to the regulating element. The term restricting element is used herein as it describes more specifically its operation, i.e. the fact that it is used for setting a highest acceptable value for a flow but in this same channel the actual control of a flow is effected by a separate regulating means.

Figure 2:
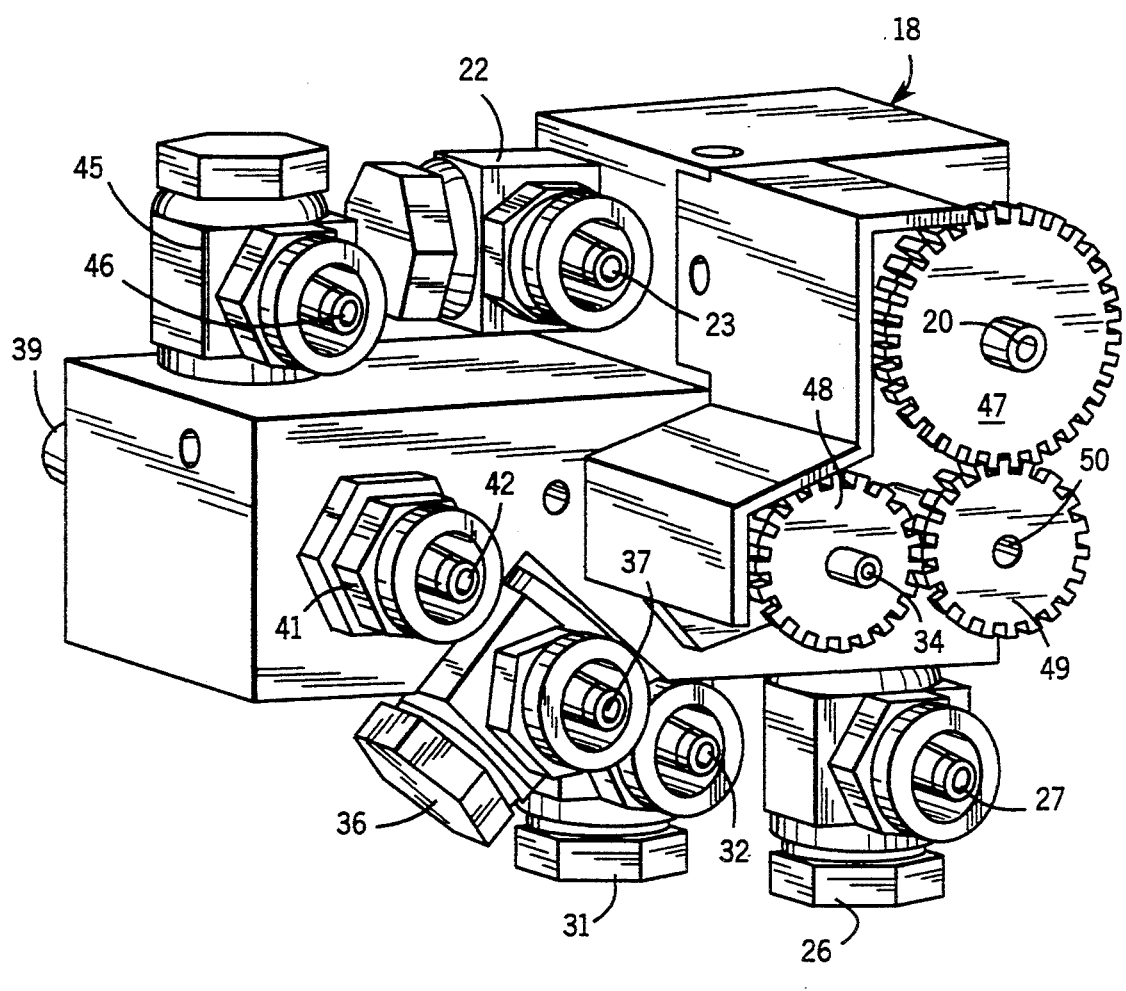
Figure 3:
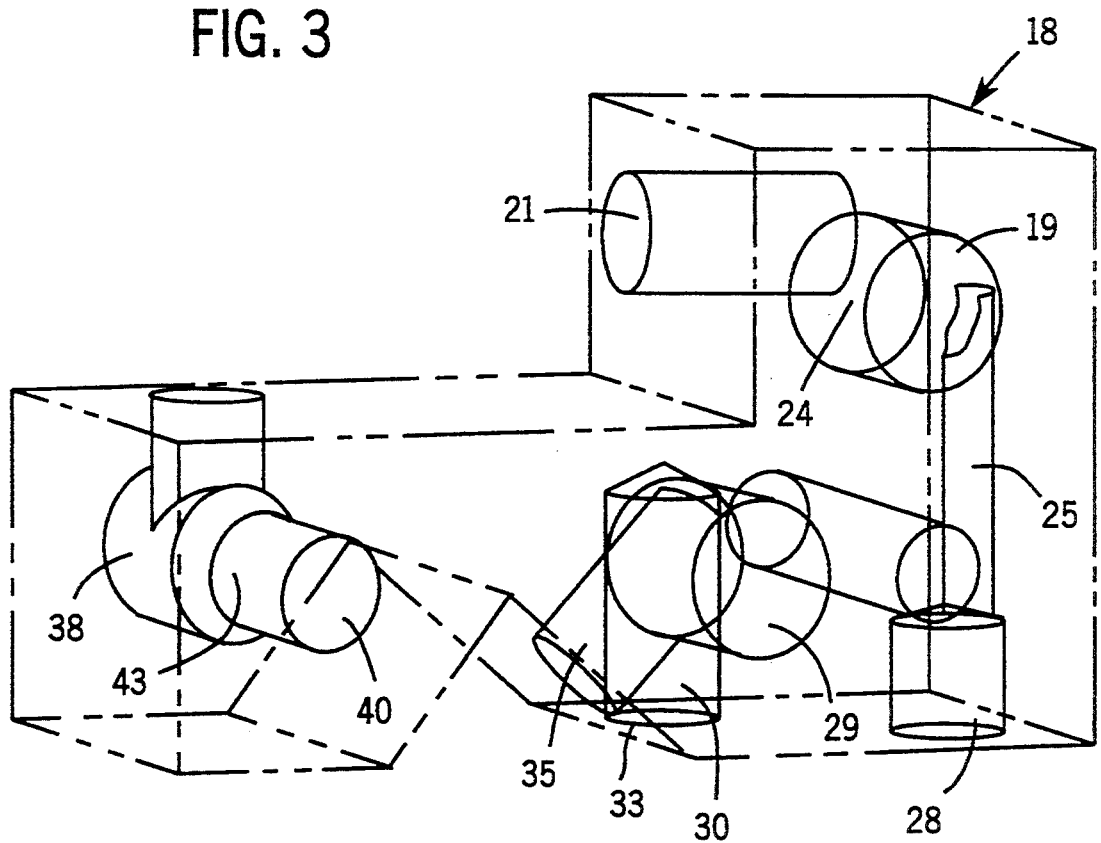

The invention will now be described in more detail with reference made to the accompanying drawings, in which FIG. 1 shows a schematic view of an apparatus of the invention, which can be used in carrying out a method of the invention, FIG. 2 shows a perspective view of the mechanical assembly of FIG. 1, FIG. 3 shows an X-ray view of a body section for the mechanical assembly of FIG. 2.

FIG. 1 illustrates a schematic view of one preferred apparatus of the invention, wherein gases flowing along two gas channels 1 and 2 are mixed with each other at a certain ratio prior to delivering a combined gas flow to be respired by a patient. From a gas source 3 flows along channel 1 a gas which is most important for the vital functions of a patient, i.e. oxygen. From a gas source 4 into channel 2 flows a gas generally used in anaesthesia examplarily described herein as nitrous oxide or "laughing" gas. Thus, a patient will receive a respiratory gas mixture, containing these two gas molecules. If necessary, some other gas can also be fed to a patient. Therefore, FIG. 1 includes yet a third gas source 5, which contains air and from which gas source a gas is delivered into a channel 6.

Gas channels 1, 2 and 6 are preferably provided with pressure regulators 7, 8 and 9 for adjusting a high pressure prevailing in gas sources 3, 4 and 5 to a desired level. The adjustment of a gas flowing in channels 1 and 2 requires regulating elements 10 and 11, which are preferably needle valves. One of the gas channels is further fitted with a flow restricting element 12, which is preferably a valve and capable of setting a maximum flow. In both channels there is preferably effected a flow measurement by means of flow measuring elements 13 and 14, which in the case of FIG. 1 are located downstream of the regulating elements.

A regulating element 10 fitted in channel 1 carrying a flow of oxygen and a flow restricting element 12 fitted in channel 2 carrying in turn a flow of nitrous oxide are linked with each other by means of a coupling assembly 15. The coupling is preferably mechanical. The coupling assembly can be used for controlling gas flows progressing in both channels. In the exemplary case shown in FIG. 1, the purpose is to use coupling assembly 15 for adjusting the oxygen flow carried in channel 1 to be suitable for a patient. Thus, the coupling assembly also automatically sets in second channel 2 a maximum acceptable flow for nitrous oxide by means of said restricting element 12. The restricting element is preferably used for adjusting the flow of nitrous oxide such that a later combined mixture of oxygen and nitrous oxide, which flows along a gas channel towards to patient, contains a sufficient amount of oxygen. Thus, as the oxygen flow increases, it is also possible to have an increased flow of nitrous oxide and, respectively, as the oxygen flow is reduced, the nitrous oxide flow will be restricted.

Channel 2 for carrying a low of nitrous oxide is provided in series both with a restricting element 12 and a regulating means or element 11, preferably disposed such that the restricting element lies upstream of the regulating element in the gas flowing direction. The operation of a regulating element differs from that of a restricting element in that said regulating element can be used for further adjusting a flow progressing through the restricting element. Thus, the restricting element allows a maximum flow possible, but the regulating element is capable of further reducing this flow from the maximum value accepted by the restricting element. The regulating element 11 located in nitrous oxide channel 2 is preferably manually adjustable, e.g. by operating a knob. When the regulating element 11 is completely open in the nitrogen oxidule channel, the developing mixture has thus a minimum oxygen content. For producing an $N_2O$ flow, both must be open. When the $N_2O$-regulating element 11 is closed, the gas mixture will be pure oxygen, however the restricting element 12 is not closed. When the oxygen regulating element is closed, the adjustment of $N_2O$ flow has no effect on the relevant gas flow.

The oxygen regulating element 10 as well as the $N_2O$ restricting element 12 are preferably needle valves, which are linear for the ratio of their flowing/opening angle and identical to each other. A variety of appropriate valves are commercially available. The characteristics of the $N_2O$ regulating element 11 are of lesser importance, but it can be a needle valve similar to regulating element 10 or restricting element 12, which are standard valves.

In a preferred solution as shown in FIG. 1, said channel 2 carrying a flow of nitrous oxide is also supplied with air arriving from a gas source 5 along a channel 6 in between restricting element 12 and regulating element 11. The junction point is provided with a selector element 17, which is preferably a valve and which selector element can be used for delivering a flow coming from either gas source 4 or 5 through regulating element 11 towards a patient.

Thus, according to selection, said selector element preferably only allows a flow from one of the gas sources to proceed to regulating element 11.

If the gas flow restricting element 12 is placed in channel 2 relative to the gas flowing direction upstream of the gas regulating element 11 and the gas selector element 17 is located between these two elements 12 and 11 such that the gas with no oxygen content is delivered to selector element 17 through restricting element 12 along with a gas containing a sufficient amount of oxygen, such as air, the restricting element 12 can thus be by-passed. Thus, in addition to pure oxygen flowing along channel 1, a patient can also be supplied with clear air. The flow of air and nitrous oxide can be controlled by using just a single regulating element 11, leading also to a simplified operating assembly.

The mechanical coupling assembly 15 is illustrated in more detail in FIG. 2. FIG. 3 reveals the internal structure for a body section 18 of said coupling assembly. The body section 18 includes a cavity 19 provided with a regulating element 10 for oxygen channel 1 with only a shaft 20 visible in FIG. 2, the action of said shaft being used for controlling the flow port of said regulating element and, thus, the flow of oxygen. Thus, oxygen flows from a gas source 3 along channel 1 to regulating element 10 through an opening 23 included in a connecting piece 22 fitted in a cavity 21 on the side of body section 18. Cavities 21 and 19 are connected by a conduit 24. From regulating element 10 leads a conduit 25 to an opening 27 included in a connecting piece 26. The connecting piece is fitted in a cavity 28 included in the body section. The oxygen gas discharges through said opening 27 of connecting piece 26 for the subsequent mixing with nitrous oxide and further along a channel 16 to a patient.

Said body section 18 of the coupling assembly includes a cavity 29 provided with said restricting element 12 for gas channel 2. The laughing gas arriving along channel 2 from gas source 4 proceeds along a conduit 33 to restricting element 12 through an opening 32 included in a connecting piece 31 fitted in a cavity 30. This restricting element is not visible in the figure, either, but nevertheless a shaft 34 used for its adjustment is shown. The gas that has passed through the restricting element discharges through an opening 37 included in a connecting piece 36 fitted in a cavity 35 towards said regulating element 11, which is fitted in a cavity 38. The only visible component of regulating element 11 is its adjusting knob 39. The regulating element receives the laughing gas through an opening 42 included in a connecting piece 41 fitted in a cavity 40. These two cavities 38 and 40 are connected by a conduit 43. From regulating element 11 the gas flows through an opening 46 included in a connecting piece 45 fitted in a cavity 44 towards a patient but, however, prior to that it is mixed with the oxygen flowing along the other channel 1.

In view of providing a mechanical coupling between flow regulating element 10 in channel 1 and flow restricting element 12 in channel 2, said shaft 20 of regulating element 11 and said shaft 34 of restricting element 34 are fitted with gears 47 and 48, preferably including cogs on the rims thereof. The gears are connected to each other through the intermediary of an idler gear 49. This idler gear carries cogs on its rim meshing with the cogs of gears 47 and 48 and is mounted on a shaft 50, whose rotation sets in rotation said shafts 20 and 34 coupled with gears 47 and 48. The rotation of shaft 50 is preferably effected from the other side of body section 18 by operating a knob, which is not shown in the figures. On the other hand, the rotation of said shafts produces a change in the flow progressing through restricting element 12 and regulating element 10, since the size of a flow port changes. Instead, the mechanical coupling of said nitrous oxide regulating valve 11 included in channel 2 has no effect, although in FIGS. 2 and 3 said regulating valve 11 is included in the same body section 18.

The diameter of the shafted gears can be varied whenever necessary. In FIG. 2, the diameter of gear 47 operating said oxygen regulating element 10 is larger than that of gear 48 operating said nitrous oxide restricting element 12. The larger the diameter of gear 47 or 48, the lesser the change effected in the size of the flow port of element 10 or 12 and hence in the flow as a result of rotating said idler gear 49. This is why the regulation of oxygen flow is effected through the action of a larger gear. The fine adjustment of nitrous oxide flow is effected separately from the mechanical coupling by means of regulating elements 11 and, thus, the adjustment of its maximum flow can be readily carried out by using a smaller gear.

The apparatus is calibrated by setting a minimum oxygen content as well as a minimum and a maximum oxygen flow. First set is a maximum oxygen flow with the oxygen regulating element fully open. This is effected by adjusting the supply pressure of oxygen by means of a regulator. This is followed by setting a minimum oxygen flow with the $N_2O$ regulating element closed and the oxygen regulating element in a position to achieve a desired minimum flow. Thereafter, a coupling assembly between the oxygen regulating element and the $N_2O$ restricting element is locked so as to immobilize the regulating and restricting elements relative to each other. The final adjustment is to set a minimum oxygen content by means of the $N_2O$ pressure. Oxygen flow is increased until it is about 1 l/min. The $N_2O$ regulating element is opened to full extent. The $N_2O$ pressure is adjusted for an $N_2O$ flow of 3 l/min.

By virtue of its structure, the apparatus is highly suitable without special arrangements also for minor flows of oxygen and $N_2O$.

In view of producing a gas mixture from gases flowing along two different channels, a gas flow is regulated by turning an adjusting knob connected to shaft 50 as well as an adjusting knob 39. Depending on the turning direction, the turning of an adjusting knob connected to shaft 50 increases or decreases a gas flow with said gear 49 included in shaft 50 rotating at the same time said gear 47, connected through the intermediary of a shaft to oxygen regulating valve 10, and said wheel 48, connected in turn through the intermediary of shaft 34 to nitrous oxide restricting element 12. When channel 1, which in this case carries a flow of oxygen, reaches a suitable gas flow, which is detected by means of a flow measuring element 13, said knob 39 is turned for adjusting a laughing gas flow progressing along channel 2 to be also suitable by using the flow-related data provided by a flow measuring element 14.

The invention is by no means limited to the above-described embodiments but various details of the invention can be modified within the scope of the annexed claims. The invention can also be exploited by mixing other gases than oxygen and nitrous oxide and possibly air at a desired ratio. Also, in the solution shown in FIG. 1, for example, the $N_2O$ restricting element 12 is located between regulating element 11 and gas source 4. However, in view of the proper function of the apparatus, the disposition or order of said elements bears no essential significance. However, the described arrangement facilitates the by-pass of a restricting element and the control of flow by using one and the same regulating element, in case it is desirable to mix e.g. air with oxygen.

A mechanical coupling between the oxygen regulating element 10 and a nitrous oxide restricting element can be effected by using a plurality of different alternatives. It can be effected by using gears fixedly mounted on valve shafts and an idler gear there between. The need for an idler gear is eliminated in case the valves are set in opposing directions. In this case, the valves are connected together directly by means of gears mounted on the shafts. The coupling can also be effected even by using a chain or a cogged belt extending between gears fixedly mounted on the shafts. The scope of this invention covers several approaches. FIG. 2 only shows one example of how to provide a mechanical coupling.

I claim:

1. An apparatus for mixing a first, ventilating gas with a second, anaesthetic gas to provide a gas mixture for supply to a patient, said apparatus insuring that the mixture contains at least a minimum content of the first gas throughout a gas supply range extending between minimum and maximum gas flow amounts of said first gas, the supply of an hypoxic gas mixture to the patient thus being prevented, said apparatus comprising:

a first gas flow channel (1) containing the first gas;

a second gas flow channel (2) containing the second gas;

a first gas flow regulator (10) interposed in said first channel for adjustably regulating the magnitude of gas flow through said first channel to a desired amount;

a second gas flow regulator (11) interposed in said second channel for adjustably regulating the magnitude of gas flow through said second channel to a desired amount;

said first and second gas flow regulators being independently operable for regulating gas flow magnitudes in said first and second gas flow channels, respectively;

a gas flow restrictor (12) interposed in said second channel for adjustably establishing the maximum magnitude of gas flow through said second channel; and coupling means (15) mechanically linking said first gas flow regulator to said gas flow restrictor for operating said gas flow restrictor each time said first gas flow regulator is operated to provide first gas flow within said gas supply range, said gas flow restrictor establishing the maximum gas flow magnitude through said second channel in accordance with the magnitude of said gas flow through said first channel, thereby providing at least a minimum content of the first gas in the mixture of the first and second gases and maintaining the ratio between the gas flow magnitude of the first gas and the maximum gas flow magnitude of the second gas within predetermined limits as the gas flow magnitude of the first gas is varied throughout said gas supply range.

2. An apparatus as set forth in claim 1 wherein said gas flow restrictor is interposed in said second channel in series with said second gas flow regulator.

3. An apparatus as set forth in claim 2 wherein said gas flow restrictor is located in said second channel upstream of said second gas flow regulator.

4. An apparatus as set forth in claim 3 further including a third gas flow channel containing a third gas comprising a ventilating gas, said third gas flow channel being connected to said second gas flow channel between said gas flow restrictor and said second gas flow regulator.

5. An apparatus as set forth in claim 1 wherein said coupling means is further defined as including gearing means for mechanically linking said first gas flow regulator and said gas flow restrictor together.

6. An apparatus as set forth in claim 5 wherein said gearing means includes an idler gear.

7. An apparatus as set forth in claim 5 wherein said first gas flow regulator and said gas flow restrictor include adjustable area, flow port means coupled to said gearing means for adjusting the area of the flow port means in accordance with the operation of the said gearing means.

8. An apparatus according to claim 1 wherein said first and second gas flow regulators comprise needle valve means.

9. An apparatus as set forth in claim 8 wherein said gas flow restrictor comprises needle valve means.

10. An apparatus as set forth in claim 1 wherein said gas flow restrictor comprises needle valve means.

11. A method for mixing a first, ventilating gas with a second, anaesthetic gas to provide a gas mixture for Supply to a patient, said method insuring that said mixture contains at least a minimum content of the first gas throughout a gas supply range extending between minimum and maximum gas flow amounts of said first gas, the supply of an hypoxic gas mixture to the patient thus being prevented, said method comprising the steps of;
flowing the first gas in a first gas flow channel;
flowing the second gas in a second gas flow channel;
adjustably regulating the magnitude of gas flow through said first channel to a desired amount;
simultaneously establishing the maximum magnitude of gas flow through said second channel in accordance with the magnitude of gas flow in said first channel whenever the gas flow through the first channel is regulated within said gas supply range, the establishment of the maximum magnitude of gas flow through said second channel providing at least a minimum content of the first gas in the mixture of the first and second gases and maintaining the ratio between the gas flow magnitude of the first gas and the maximum gas flow magnitude of the second gas within predetermined limits as the gas flow magnitude of the first gas is varied throughout said supply gas range; and
adjustably regulating the magnitude of gas flow through said second channel to a desired amount;
the adjustable regulation of the gas flow magnitudes in said first and second gas flow channels, respectively, being carried out independently of each other.

12. A method as set forth in claim 11 further defined as regulating the magnitude of the gas flow through said second channel at a point in said second gas flow channel downstream of a point at which the maximum magnitude of gas flow through said second channel is established.

13. A method according to claim 11 further defined as flowing a first gas comprising an oxygen containing gas in said first gas flow channel and a second gas comprising a nitrous oxide containing gas through said second gas flow channel.

14. A method as set forth in claim 11 further including the step of flowing a third gas comprising a ventilating gas in a third gas flow channel and supplying the third gas to the second gas flow channel.

15. A method as set forth in claim 14 further defined as supplying the third gas to the second gas flow channel after establishing the maximum magnitude of the gas flow of the second gas in the second gas flow channel.

16. An apparatus for mixing a first, ventilating gas with a second, anaesthetic gas to provide a gas mixture for supply to a patient, said apparatus insuring that the mixture contains at least a minimum content of the first gas so that the supply of an hypoxic gas mixture to the patient is prevented, said apparatus comprising:
a first gas flow channel (1) containing the first gas;
a second gas flow channel (2) containing the second gas;
a first gas flow regulator (10) interposed in said first channel for adjustably regulating the magnitude of gas flow through said first channel to a desired amount;
a second gas flow regulator (11) interposed in said second channel for adjustably regulating the magnitude of gas flow through said second channel to a desired amount;
said first and second gas flow regulators being independently operable for regulating gas flow magnitudes in said first and second gas flow channels, respectively;
a gas flow restrictor (12) interposed in said second channel in series with said second gas flow regulator, said gas flow restrictor being located in said second channel upstream of said second gas flow regulator and adjustably establishing the maximum magnitude of gas flow through said second channel; and
coupling means (15) mechanically linking said first gas flow regulator to said gas flow restrictor for establishing the maximum gas flow magnitude through said second channel in accordance with the magnitude of gas flow through said first channel for providing at least a minimum content of the first gas in the mixture of the first and second gases and for maintaining the ratio between the gas flow magnitude of the first gas and the maximum gas flow magnitude of the second gas within predetermined limits as the gas flow magnitude of the first gas is varied.

17. An apparatus as set forth in claim 16 wherein said coupling means is further defined as including gearing means for mechanically linking said first gas flow regulator and said gas flow restrictor together.

18. An apparatus as set forth in claim 17 wherein said gearing means includes an idler gear.

19. An apparatus as set forth in claim 17 wherein said first gas flow regulator and said gas flow restrictor include adjustable area, flow port means coupled to said gearing means for adjusting the area of the flow port means in accordance with the operation of the said gearing means.

20. An apparatus according to claim 16 wherein said first and second gas flow regulators comprise needle valve means.

21. An apparatus as set forth in claim 19 wherein said gas flow restrictor comprises needle valve means.

22. An apparatus as set forth in claim 16 wherein said gas flow restrictor comprises needle valve means.

23. An apparatus as set forth in claim 16 further including a third gas flow channel containing a third gas comprising a ventilating gas, said third gas flow channel being connected to said second gas flow channel between said gas flow restrictor and said second gas flow regulator.

24. A method for mixing a first, ventilating gas with a second, anaesthetic gas to provide a gas mixture for supply to a patient, said method insuring that said mixture contains at least a minimum content of the first gas so that the supply of an hypoxic gas mixture to the patient is prevented, said method comprising the steps of:

flowing the first gas in a first gas flow channel;

flowing the second gas in a second gas flow channel;

adjustably regulating the magnitude of gas flow through said first channel to a desired amount while establishing the maximum magnitude of gas flow through said second channel in accordance with the magnitude of gas flow through the first channel to provide at least a minimum content of the first gas in the mixture of the first and second gases and for maintaining the ratio between the gas flow magnitude of the first gas and the maximum gas flow magnitude of the second gas within predetermined limits as the gas flow magnitude of the first gas is varied; and adjustably regulating the magnitude of gas flow through said second channel to a desired amount after the maximum magnitude of gas flow through said second channel has been established;

the adjustable regulation of the gas flow magnitudes in said first and second gas flow channels, respectively, being carried out independently of each other.

25. A method as set forth in claim 18 further defined as simultaneously regulating the magnitude of the gas flow through said first channel and establishing the maximum magnitude of gas flow through said second channel.

26. A method according to claim 18 further defined as flowing a first gas comprising an oxygen containing gas in said first gas flow channel and a second gas comprising a nitrous oxide containing gas through said second gas flow channel.

27. A method as set forth in claim 18 further including the step of flowing a third gas comprising a ventilating gas in a third gas flow channel and supplying the third gas to the second gas flow channel.

28. A method as set forth in claim 22 further defined as supplying the third gas to the second gas flow channel after establishing the maximum magnitude of the gas flow of the second gas in the second gas flow channel.

* * * * *